(12) United States Patent
Pöchlauer et al.

(10) Patent No.: US 6,417,377 B1
(45) Date of Patent: Jul. 9, 2002

(54) PROCESS FOR PREPARING ENANTIOMER-ENRICHED AMINO- AND HYDROXYFURANONES

(75) Inventors: Peter Pöchlauer, Linz (AT); Peter Riebel, Ruhstorf/Rott (DE); Herbert Mayrhofer, Engerwitzdorf; Irma Wirth, Enns, both of (AT)

(73) Assignee: DSM Fine Chemicals Austria Nfg GmbH & Co KG, Linz (AT)

( * ) Notice: Subject to any disclaimer, the term of this patent is extended or adjusted under 35 U.S.C. 154(b) by 0 days.

(21) Appl. No.: 10/044,908

(22) Filed: Jan. 15, 2002

(30) Foreign Application Priority Data

Jan. 16, 2001 (AT) ................................. 61/2001

(51) Int. Cl.$^7$ ..................... C07D 307/60; C07D 307/66
(52) U.S. Cl. ..................... 549/313; 549/319; 549/321
(58) Field of Search ................................. 549/313, 319, 549/321

(56) References Cited

FOREIGN PATENT DOCUMENTS

JP 63-93774 * 4/1988

OTHER PUBLICATIONS

Patent Abstracts of Japan, vol. 12, No. 333, Section No. 526, p. 49 (1988) –Abstract of JP 63–093774.

* cited by examiner

*Primary Examiner*—Bernard Dentz
(74) *Attorney, Agent, or Firm*—Wenderoth, Lind & Ponack, LLP

(57) ABSTRACT

A process for the preparation of enantiomer-enriched aminofuranones and hydroxyfuranones in which an enantiomer-enriched cyanohydrin is acylated by an acylating agent, then cyclized at 40 to 90° C. in the presence of zinc or a zinc compound to the corresponding enantiomer-enriched aminofuranone, which is converted where appropriate by acid hydrolysis into the corresponding enantiomer-enriched hydroxyfuranone.

5 Claims, No Drawings

PROCESS FOR PREPARING ENANTIOMER-ENRICHED AMINO- AND HYDROXYFURANONES

Amino- and hydroxyfuranones are, because of their biological activities, important starting materials for the preparation of compounds with an antibiotic, hypotensive or antitumor effect, and of fungicides, insecticides etc.

Most amino- and hydroxyfuranones having a chiral center are, however, employed only in the form of their racemates. However, normally only one enantiomer in a racemic mixture of a biologically active compound shows the desired effect.

Some syntheses for optically active hydroxyfuranones (tetronic acids) starting from enantiopure cyanohydrins by use of the Blaise reaction have already been described, it being observed that there is partial racemization on synthesis of compounds susceptible to racemization, such as, for example, 5-aryl-4-hydroxytetronic acids (Effenberger, Tetrahedron Asymmetry 9 (1998) 817–825).

Optically active tetronic acids have to date usually been synthesized by Dieckmann cyclization starting from enantiopure hydroxy acids (Effenberger, Tetrahedron Asymmetry 9 (1998) 817–825).

Other methods, starting from hydroxy esters, require low reaction temperatures down to −78° C. (Witiak, J. Org. Chem. 1990, 55, 1112–1114).

Momose, Heterocycles, Vol. 51, 6, 1999 describes the synthesis of optically active 4-hydroxy-2(5H)-furanone derivatives (tetronic acids) by reaction of 2-acyloxy esters with zinc to form the Reformatsky compound and intramolecular ring closure. This is associated with a side reaction in which the resulting alcohol (on ring closure) destroys the Reformatsky compound and consequently the maximum yields are only 50% (Brandange, Acta Chem. Scand., 1995, 49, 922–928).

It is also known from the literature that tetronic acids can be obtained by acid hydrolysis on 4-aminofuranones (C. Veronese, Heterocycles, Vol. 32, No. 11, 1991; Nishide, Tetrahedron Vol. 50, No. 28, 8337–8346, 1994).

The preparation of racemic 4-amino-2(5H)-furanone (aminofuranones), derivatives of cyanohydrins by intermolecular reaction with magnesium enolates is described. In addition, cyclization reactions are carried out on acyloxy nitrites with lithium amides at −78° C. or with NaH in THF at the reflux temperature. However, these reactions are applicable only to aldehyde cyanohydrins (Hiyama, Bull. Chem. Soc. Jpn., 60, 2139–2150, 1987) and only on use of a low reaction temperature is it possible to react enantiopure cyanohydrins without racemization (Ohta, Tetrahedron Letters, Vol. 29, No. 52, pp 6957–6960, 1988). The loss of enantiopurity in cyclizations using NaH is described, for example, in T. Ross Kelly, Tetrahedron Letters, Vol. 26, 18, 2173–2176, 1985.

The cyclization of acyloxy nitrites with zinc at about 60° C. is described for racemic cyanohydrins in yields of about 90% in Chem. Abstr. 109: 110244 (JP 63093774).

It was an object of the present invention to find a process which provides optically active, enantiomer-enriched aminofuranones and subsequently optically active, enantiomer-enriched hydroxyfuranones in high yields and without racemization.

Unexpectedly, it has been possible to find a process by which enantiomer-enriched cyanohydrins are also reacted in good yields after acylation by intramolecular Reformatsky reaction with zinc at 60° C. without racemization to give optically active aminofuranones, which are themselves important compounds (Hiyama, Tetrahedron Letters, Vol. 26, No. 20, 2459–2462, 1985).

The resulting aminofuranones can further be converted into optically active hydroxyfuranones.

The present invention accordingly relates to a process for the preparation of enantiomer-enriched aminofuranones and hydroxyfuranones, which comprises a) acylating an optically active cyanohydrin using an acylating agent, then
b) at 40 to 90° C. cyclizing, in the presence of zinc or a zinc compound, to the corresponding enantiomer-enriched aminofuranone, which is
c) where appropriate converted by acid hydrolysis into the corresponding enantiomer-enriched hydroxy-furanone.

In stage a) there is acylation of optically active cyanohydrins. Suitable starting compounds in this case are optically active cyanohydrins which are obtained, for example, by reacting an aldehyde or a ketone, a cyanide group donor and a hydroxynitrile lyase.

Aldehydes mean in this connection aliphatic, aromatic or heteroaromatic aldehydes. Aliphatic aldehydes in this connection are saturated or unsaturated aliphatic, straight-chain, branched or cyclic aldehydes. Preferred aliphatic aldehydes are straight-chain aldehydes with, in particular, 2 to 18 C atoms, preferably from 2 to 12, which are saturated or mono- or polyunsaturated. The aldehyde may moreover have both C—C double bonds and C—C triple bonds. The aldehyde may be unsubstituted or be substituted by groups which are inert under the reaction conditions, for example by optionally substituted aryl or heteroaryl groups such as phenyl or indolyl groups, by halogen, ether, alcohol, acyl, carboxylic acid, carboxylic ester, nitro or azido groups.

Examples of aromatic or heteroaromatic aldehydes are benzaldehyde and variously substituted benzaldehydes such as, for example, 3,4-difluorobenz-aldehyde, 3-phenoxybenzaldehyde, 4-fluoro-3-phenoxy-benzaldehyde, also furfural, anthracene-9-carbaldehyde, furan-3-carbaldehyde, indole-3-carbaldehyde, naphthalene-1-carbaldehyde, phthalaldehyde, pyrazole-3-carbaldehyde, pyrrole-2-carbaldehyde, thiophene-2-carbaldehyde, isophthalaldehyde etc.

Ketones are aliphatic, aromatic or hetero-aromatic ketones in which the substituents on the carbonyl carbon atom are not the same. Aliphatic ketones means saturated or unsaturated, straight-chain, branched or cyclic ketones. The ketones may be saturated or mono- or polyunsaturated. They may be unsubstituted or be substituted by groups which are inert under the reaction conditions, for example by optionally substituted aryl or heteroaryl groups such as phenyl or indolyl groups, by halogen, ether, alcohol, acyl, carboxylic acid, carboxylic ester, nitro or azido groups.

Examples of aromatic or heteroaromatic ketones are acetophenone or indolylacetone etc.

The optically active cyanohydrins which are employed contain the (S) or (R) form in a proportion of more than 95% and can be represented by formula (I) as follows:

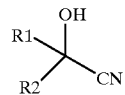

R1 and R2 are derived from the abovementioned aldehydes and ketones and thus are preferably H, it being possible for only one of the two radicals R1 and R2 to be H; and linear, branched or cyclic $C_2$–$C_{18}$-alkyl, $C_2$–$C_{18}$-alkylene or $C_2$–$C_{18}$-alkylidene, each of which may optionally be substituted one or more times by halogen, ether, alcohol, acyl, carboxylic acid, carboxylic ester, nitro or azido groups or by optionally substituted aryl or heteroaryl groups, or are optionally substituted aralkyl, aryl or heteroaryl.

Particular preference is given to optically active aliphatic and aromatic cyanohydrins such as, for example, (R)- or (S)-3-phenoxybenzaldehyde cyanohydrin, (R)- or (S)-4-fluoro-3-phenoxybenzaldehyde cyanohydrin, (R)- or (S)-3,4-difluorobenzaldehyde cyanohydrin, (R)- or (S)-2-hydroxy-2,3-dimethylbutanonitrile, (R)- or (S)-2-hydroxy-2-methylpentanonitrile, (R)- or (S)-2-hydroxynonanonitrile, (R)- or (S)-2-hydroxy-2-methyl-phenylacetonitrile, (R)- or (S)-mandelonitrile.

The acylation takes place under the usual conditions known from the prior art, for example from Takefumi Momose, Heterocycles, Vol. 51, No. 6, 1999. According to this, the reaction temperature is preferably between 20 and 50° C. The molar ratio of cyanohydrin to acylating agent is preferably between 1:1 and 1:3. Examples of suitable solvents are optionally halogenated hydrocarbons such as, for example, cyclohexane, xylene, toluene, chloroform, dichloromethane, chlorobenzene, ethers, esters, pyridine, etc. or mixtures thereof. The acylation preferably takes place with basic catalysis using pyridine or triethylamine etc. by means of a halo carbonyl halide of the formula IIa

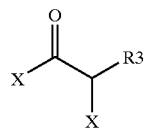

or halo carboxylic anhydride of the formula IIb

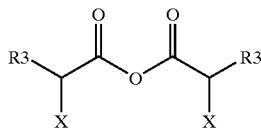

where R3 is an aliphatic, linear or branched $C_1$ to $C_{18}$-alkyl radical or an aryl radical with 6 to 20 C atoms and X is a halide from the group of fluorine, bromine, chlorine and iodine, resulting in compounds of the formula (III)

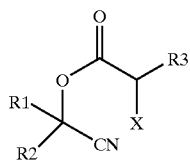

in which R1, R2, R3 and X are as defined above.

In step b), the acylation is followed by cyclization of the compound of the formula III in the presence of zinc, which may be activated, for example, with iodine or copper. It is preferred to use only Zn. The cyclization temperatures are 40–90° C., preferably 50 to 75° C. Zn is employed in this case in an amount of 1–3 equivalents, preferably of 1 to 1.5 equivalents. After a reaction time of 0.5–3 hours, the corresponding aminofuranones of the formula (IV)

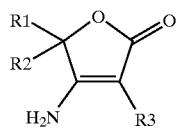

in which R1, R2 and R3 are as defined above are obtained.

Suitable solvents are aliphatic or aromatic hydrocarbons such as, for example, cyclohexane, xylene, toluene, benzene, ethers such as, for example, diethyl ether, methyl tert-butyl ether, diisopropyl ether, dibutyl ether, tetrahydrofuran, etc. or mixtures thereof.

The aminofuranones can be isolated from the reaction mixture, for example by extraction, removal of the solvent by distillation etc., resulting in the desired aminofuranones in yields of up to more than 90% and in an enantiopurity of >90%, without a racemization reaction having occurred.

The aminofuranones can, if required, be converted into the corresponding optically active hydroxyfuranones (step c), it being possible for this to take place after isolation of the particular aminofuranone or else, however, without isolation of the aminofuranone from the reaction mixture, immediately following step b).

Step c), the acid hydrolysis, is carried out in analogy to the prior art, and takes place, for example, in THF/HCl, or by basic hydrolysis. The hydrolysis is preferably carried out in THF/HCl, particularly preferably with 15–20% strength hydrochloric acid.

The corresponding hydroxyfuranones are then isolated from the reaction mixture in a conventional way, for example by extraction, removal of the solvent by distillation, and obtained in high yields of up to 75%, and in an enantiopurity of >90%.

The process of the invention is distinguished by being particularly advantageous compared with other cyclization reactions known from the prior art, because the cyclization by intramolecular Reformatsky reaction with zinc or zinc compounds can be applied both to aldehyde cyanohydrins and ketone cyanohydrins, and no extreme reaction temperatures are necessary, and no racemization is observed even with 5-aryl-4-hydroxy-tetronic acids.

EXAMPLE 1

Acylation of Cyanohydrins 6.0 g (45.1 mmol) of (S)-2-hydroxyphenylacetonitrile with 98.8% ee were dissolved in 25 ml of dichloromethane and cooled to 1° C. Then 11.7 g (54.1 mmol) of 2-bromopropionyl bromide were added dropwise over the course of 10 minutes. Addition of 0.27 g (2.2 mmol) of dimethylaminopyridine was followed by dropwise addition of 5.5 g (54.1 mmol) of triethylamine at a temperature below 5° C. After stirring at 5° C. for 1.75 hours, the mixture was warmed to room temperature and then stirred for 22 hours. This was followed by extraction with 55 ml of water and separation of the phases. The organic phase was subsequently extracted twice with 30 ml of saturated sodium bicarbonate solution and once with saturated sodium chloride solution. Finally, the organic phase was dried with sodium sulfate and the solvent was completely removed by distillation.

10.3 g (85.2% yield) of (S)-2-(2-bromopropionyloxy) phenylacetonitrile remained as residue.

EXAMPLE 2
Cyclization of Optically Active Cyanohydrins to the Aminofuranones The zinc used for the activation was washed successively with 10% strength hydrochloric acid, acetone and diethyl ether and dried by stirring under reduced pressure.

0.40 g (6.12 mmol) of activated zinc were weighed under argon into the reaction flask, and 2 ml of tetrahydrofuran were added. This was followed by heating to about 65° C. under an inert argon atmosphere. A solution of 5.56 mmol of the appropriate optically active acyloxy nitrile (see Table 1) in 1 ml of THF was added dropwise over the course of 15 min. After stirring at about 65° C. for 2 hours, the mixture was cooled and, at a temperature below 0° C., 2 ml of saturated ammonium chloride solution were added dropwise. This was followed by warming to room temperature, addition of ethyl acetate and separation of the phases. The aqueous phase was extracted once more with ethyl acetate. The organic phases were dried and freed of solvent. Enantiomer analysis took place by GC on a cyclodextrin column.

TABLE 1

| Acyloxy nitrile | ee | Aminofuranone | ee |
| --- | --- | --- | --- |
| (S)-2-(2-bromopropionyl-oxy)phenylacetonitrile | >98% | (5S)-4-amino-3-methyl-5-phenyl-2(5H)-furanone | 96% |
| (S)-2-(2-bromopropionyl-oxy)-non anonitrile | 93% | (5S)-4-amino-3-methyl-5-heptyl-2(5H)-furanone | 93% |
| (S)-2-(2-bromopropionyl-oxy)-2-phenylpropionitrile | 96% | (5S)-4-amino-3,5-dimethyl-5-phenyl-2(5H)-furanone | 96% |

EXAMPLE 3
Cyclization of Optically Active Cyanohydrins to the Hydroxyfuranones The zinc used for the activation was washed successively with 10% strength hydrochloric acid, acetone and diethyl ether and then dried.

0.40 g (6.12 mmol) of activated zinc were weighed under argon into the reaction flask, and 2 ml of tetrahydrofuran were added. This was followed by heating to about 65° C under an inert argon atmosphere. A solution of 5.56 mmol of the appropriate optically active acyloxy nitrile (see Table 2) in 1 ml of THF was added dropwise over the course of 15 min. After stirring at about 65° C for 2 hours, the mixture was cooled and, at a temperature below 0° C., 2 ml of saturated ammonium chloride solution were added dropwise, and the mixture was diluted with 4 ml of water and 4 ml of tetrahydrofuran. This was followed by warming to room temperature and separation of the phases. Part of the solvent was removed from the organic phase by distillation, and 5 ml of 1:1 hydrochloric acid were added. Hydrolysis was then carried out at 60–70° C. for 24 hours.

The reaction mixture was then freed of solvent, and the residue was mixed with 20 ml of distilled water. The aqueous phase was adjusted to pH 9.5 with 2 M sodium hydroxide solution. After extraction with ethyl acetate and phase separation, the aqueous phase was adjusted to pH 1 with 10% strength hydrochloric acid and extracted three times with ethyl acetate. The organic phases were dried and freed of solvent. The enantiopurity was determined by GC on a cyclodextrin column.

TABLE 2

| Acyloxy nitrile | ee | Hydroxyfuranone | Yld | ee |
| --- | --- | --- | --- | --- |
| (S)-2-(2-bromopropionyl-oxy)phenylacetonitrile | >98% | (5S)-4-hydroxy-3-methyl-5-phenyl-2(5H)-furanone | 70% | 93% |
| (s)-2-(2-bromopropionyl-oxy)nonanonitrile | 93% | (5S)-4-hydroxy-3-methyl-5-heptyl-2(5H)-furanone | 71% | 91% |
| (S)-2-(2-bromopropionyl-oxy)-2-phenylpropionitrile | 96% | (5S)-4-hydroxy-3,5-dimethyl-5-phenyl-2(5H)-furanone | 75% | 96% |

What is claimed is:

1. A process for the preparation of enantiomer-enriched aminofuranones and hydroxyfuranones, which comprises
   a) acylating an enantiomer-enriched cyanohydrin using an acylating agent, then
   b) at 40 to 90° C. cyclizing, in the presence of zinc or a zinc compound, to the corresponding enantiomer-enriched aminofuranone, which is
   c) where appropriate converted by acid hydrolysis into the corresponding enantiomer-enriched hydroxy-furanone.

2. A process as claimed in claim 1, wherein an optically active aldehyde cyanohydrin or ketone cyanohydrin which contains the (S) or (R) form in a proportion of more than 95% is employed as starting compound.

3. A process as claimed in claim 1, wherein acylation of the cyanohydrin results in the compound of the formula

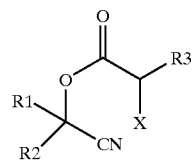

in which one of the two radicals R1 or R2 can be H; or R1 and R2 are identical or different and are a linear, branched or cyclic $C_2$–$C_{18}$-alkyl group, $C_2$–$C_{18}$-alkylene group or $C_2$–$C_8$-alkylidene group, each of which may optionally be substituted one or more times by halogen, ether, alcohol, acyl, carboxylic acid, carboxylic ester, nitro or azido groups or by optionally substituted aryl or heteroaryl groups, or are an optionally substituted aralkyl, aryl or heteroaryl, R3 is an aliphatic, linear or branched $C_1$ to $C_8$-alkyl radical or an aryl radical with 6 to 20 C atoms and X is a halide from the group of fluorine, bromine, chlorine and iodine.

4. A process as claimed in claim 1, wherein the cyclization in step b) takes place in the presence of zinc, which may optionally be activated by iodine or copper, at 40–90° C., resulting in compounds of the formula (IV)

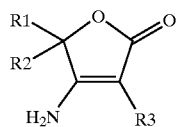

in which R1, R2 and R3 are as defined above, in yields of up to more than 90% and in an enantiopurity of >90%.

5. A process as claimed in claim 1, wherein the aminofuranones obtained in step c) are converted by acid hydrolysis into the corresponding hydroxy-furanones, it being possible for the hydrolysis to take place after isolation of the corresponding aminofuranone or directly following the cyclization in step b).

* * * * *